United States Patent [19]

Verbrugge et al.

[11] 4,025,562

[45] May 24, 1977

[54] PROCESS FOR THE PREPARATION OF MACROCYCLIC KETONES

[75] Inventors: Pieter A. Verbrugge; Willy Brunmayer-Schilt, both of Amsterdam, Netherlands

[73] Assignee: Shell Oil Company, Houston, Tex.

[22] Filed: Nov. 4, 1974

[21] Appl. No.: 520,768

[30] Foreign Application Priority Data

Nov. 14, 1973 United Kingdom ............ 52775/73

[52] U.S. Cl. ........................ 260/586 P; 260/586 R; 260/586 M; 260/617 H; 260/617 M; 260/648 D; 260/666 A

[51] Int. Cl.² .................... C07C 45/00; C07C 45/16

[58] Field of Search ...... 260/648 D, 666 A, 617 H, 260/617 M, 586 R, 586 P, 586 C, 586 M

[56] References Cited

UNITED STATES PATENTS

| | | | |
|---|---|---|---|
| 2,526,171 | 10/1950 | Stoll | 260/586 M |
| 3,586,720 | 6/1971 | Knepper et al. | 260/586 P |

FOREIGN PATENTS OR APPLICATIONS

| | | | |
|---|---|---|---|
| 634,024 | 2/1962 | Italy | 260/586 M |
| 39-26966 | 11/1964 | Japan | 260/586 M |
| 37-16708 | 10/1962 | Japan | 260/586 M |
| 119,620 | 12/1925 | Switzerland | 260/586 M |
| 1,205,047 | 10/1970 | United Kingdom | 260/586 M |

OTHER PUBLICATIONS

Bach, "Tetra. Lett.," No. 56, pp. 5841–5844 (1968) Pergamon Press.
Sharma et al., "J. Org. Chem.", 32, p. 241–244, (1967).
Muhlstadt et al., "Chem. Ber.," 100, pp. 223–227 (1967).
Mozacki et al., "Can. J. of Chem.," vol. 44, pp. 1021–1026 (1966).
Makosza et al., "Tetra. Letters", No. 53, pp. 4659–4662 (1969).
Freser et al., "Reagents For Org. Syn.", vol. 4, pp. 27–31 (1974).

*Primary Examiner*—Norman Morgenstern

[57] ABSTRACT

Saturated cyclic ketones having 12 to 20 carbon atoms in the ring, such as muscone, are prepared by (a) the reaction of a cyclic olefin with a dihalocarbene, (b) dehalogenation of the resulting dihalobicylic compound to form a cyclic allene, (c) hydration and oxidation of the cyclic allene to form an unsaturated cyclic ketone, and (d) conversion of the unsaturated cyclic ketone to a saturated cyclic ketone, with optional introduction of an alkyl substituent.

12 Claims, No Drawings

PROCESS FOR THE PREPARATION OF MACROCYCLIC KETONES

This invention relates to a process for the preparation of cyclic ketones and in particular to the preparation of certain macrocyclic ketones which are of interest as aroma chemicals.

The synthetic routes which have been used up to now for the preparation of such cyclic ketones have been based mainly on the ring closure of α,ω-disubstituted derivatives. However the starting materials for such preparations are, in general, not easily accessible. Alternative procedures based on right expansions or contractions have been suggested recently, but these involve a large number of individual steps, which would tend to preclude their use on a large scale.

The process of the present invention offers a convenient route to certain cyclic ketones using readily available starting materials.

Accordingly the invention provides a process for the preparation of cyclic ketones having the general formula:

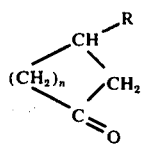 (I)

wherein R represents a hydrogen atom or an alkyl group, suitably of 1 to 6 carbon atoms, preferably methyl, and n is an integer from 9 to 17, which process comprises the following steps:

a. reaction of a cyclic olefin of formula:

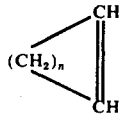 (II)

with a dihalocarbene, in the presence of an onium salt as catalyst.

b. dehalogenation of the dihalobicyclic compound thus formed to give a cyclic allene of formula:

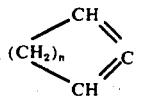 (III)

c. hydration and oxidation of this cyclic allene to an unsaturated ketone, and d. conversion of the double bond of the unsaturated ketone to a single bond, optionally with introduction of an alkyl substituent.

The dihalocarbene for reaction with the cyclic olefin of formula II in step (a) is suitably generated in situ by the reaction of a haloform, for example chloroform or bromoform, with an alkali metal hydroxide, e.g. sodium hydroxide. In a preferred procedure the reaction is carried out in a two-phase aqueous/organic solvent system using, for example a quaternary ammonium, quaternary phosphonium or ternary sulphonium salt as catalyst, as described in our co-pending British application No. 22911/72. Suitable organic solvents are halogenated hydrocarbons such as an excess of the haloform, or dichloromethane, and particularly suitable catalyst are tri-sec-octyl methylammonium chloride
tetramethyl phosphonium iodide
sec-hexadecyl sec-dodecyl ethylsulphonium ethylsulphate di-dodecyl ethylsulphonium ethylsulphate
di-hexadecyl ethylsulphonium ethylsulphate Suitable reaction temperatures are generally from 25°–60° C. The reaction may optionally be carried out in the presence of a non-ionic surface-active agent as described in our copending British application No. 52744/73.

The dehalogenation step (b) may be carried out by the use of a suitable metal selected from Group II of the Periodic Table, for example magnesium or zinc. For the most satisfactory results the metal should preferably be activated before use in step (b). Suitable activation procedures are for example treatment of the metal with sodium amalgam, or with an elemental halogen such as bromine or iodine followed by heating at 300°–400° C. Alternatively the dehalogenation may be carried out using an organometallic derivative such as a lithium alkyl, preferably butyllithium.

The term hydration is used in step (c) in a general sense to include any procedure which results overall in a molecule of water being added to a molecule of the cyclic allene. The hydration as performed in step (c) may be carried out by converting the allene to an unsaturated alcohol of formula:

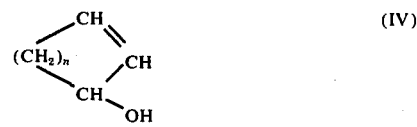 (IV)

in the presence of a mercury (II) compound, e.g. $H_aSO_4$ in the presence of a sulphuric acid. In a more preferred procedure, described in our copending British application No. 24069/74, the hydration is carried out in the presence of mercuric nitrate and in the absence of added mineral acid. The hydration may also be carried out in a modified two-stage procedure by reacting the cyclic allene first with formic acid in the presence of the mercury(II) compound and then hydrolysing the formate ester thus formed under basic conditions.

The oxidation of the unsaturated alcohol of formula IV to the corresponding unsaturated ketone may be carried out by any of the methods usually employed for oxidizing or dehydrogenating alcohols, for example by the use of a chromium(VI) compound such as an alkali metal dichromate under acidic conditions, or a manganese(IV) compound such as manganese dioxide under neutral conditions.

Another procedure which may be employed for converting the allene of formula II to the unsaturated ketone comprises first reacting the allene with borine ($B_2H_6$) and then simultaneously hydrolysing and oxidizing the product formed using, for example, an alkaline hydrogen peroxide solution.

The unsaturated ketone may be converted to the unsaturated ketone of formula I wherein R represents a hydrogen atom, by hydrogenation. Those compounds wherein R represents an alkyl group may be obtained by treatment of the unsaturated ketone with a metal alkyl derivative suitably an alkyl Grignard reagent, in the presence of a copper (I) halide, suitably the chloride bromide or iodide, as catalyst, followed by hydrolysis.

The process of the invention is of special interest for the preparation of compounds of formula I wherein $n$ is from 10 to 14, i.e. for the preparation of ketones containing a $C_{13}$ to $C_{17}$ ring and in particular the $C_{15}$ derivatives, especially 3-methylcyclopentadecanone. This compound, commonly known as muscone is important commercially as an aroma chemical.

The starting material of formula II for the preparation of the $C_{15}$ derivatives by the process of the invention is cyclotetradecene. This cyclic olefin may be prepared by dimerising cycloheptene in the presence of a suitable catalyst, preferably a supported transition metal oxide e.g. $Re_2O_7$, or $MoO_3$, preferably promoted by CoO, followed by partial hydrogenation of the cyclotetradeca-1,8-diene thus formed.

The invention is further illustrated in the following examples.

EXAMPLE I

Addition of dihalocarbenes to cyclic olefins a. 15,15-dichlorobicyclo[12.1.0]pentadecane Cyclotetradecene (4.0 g), chloroform (18 ml), 50% aqueous sodium hydroxide solution (22 ml), dichloromethane (5 ml), n-octane (1 ml) and tetramethylphosphonium iodide (0.01 g) were stirred together at 35° C for 3 hours. At the end of this period the conversion of starting material to the desired product was found by GLC to be 100%.

b. 15,15-dibromobicyclo[12.1.0]pentadecane

Cyclotetradecene (40 g), bromoform (75.9 g), 50% aqueous sodium hydroxide solution (300 ml), dichloromethane (20 ml), tri-sec-octyl methylammonium chloride (1 drop) and 1 drop of a long-chain alcohol ethoxylate of the structure $[C_{14-15}]$ $[OC_2]_{11}$—OH (Dobanol 45 + 11 EO, Shell Chemicals) were stirred together at 40° C for 7 hours. The organic layer was separated and the volatile organic components removed under reduced pressure. The residue was dissolved in pentane and the solution was stirred with active charcoal (Norit). The solution was filtered and the pentane removed under reduced pressure to give the required product in almost 100% yield.

c. 13,13-dichlorobicyclo[10.1.0]tridecane

Cyclododecene (41.5 g), chloroform (225 ml), 50% aqueous sodium hydroxide solution (275 ml), dichloroethane (60 ml), sec-hexadecyl sec-dodecyl ethylsulphonium ethylsulphate (0.3 g) and n-octane (12 ml) were stirred together at ambient temperature for 10 hour. The product was recovered in a similar manner to that described in Example I(b) (yield 98%)

EXAMPLE II

Cyclic allene formation a. 15,15Dibromobicyclo[12.1.0]pentadecane (6.6 g, prepared as in Example I(b) was dissolved in ether (16 ml) and the solution cooled to −30° to −40° C under an atmosphere of dry nitrogen. A mixture of ether (13 ml) and 20% butyl lithium in hexane (15 ml) was added to this solution over a period of one hour. The mixture was then stirred for a further 30 minutes at −30° to −40° C. The excess butyl lithium in the mixture was decomposed by careful addition of water and the aqueous mixture was separated. The organic layer was then dried and evaporated to yield 3.34 g of a product containing 90% allene. The required allene was obtained in 80% yield.

When the above procedure was repeated using 15,15-dichlorobicyclo[12.1.0]pentadecane the yield of allene was 64%.

b. Metallic magnesium (0.4 g) was treated with a small drop of liquid bromine or a small crystal of iodine dissolved in ether or tetrahydrofuran under an atmosphere of dry nitrogen. When the coloration due to the halogen was no longer visible the solvent was flushed away by heating in a stream of nitrogen. The residue was heated to 300°–400° C for 15 minutes under nitrogen and then cooled to room temperature. A solution of 15,15-dibromobicyclo[12.1.0]pentadecane (1.0 g) in the tetrahydrofuran was added to the activated metal and the mixture was allowed to react at 20° C. 100% Conversion of the starting material with selectivity to the desired allene of 99% was obtained using a reaction time of 1 hour.

EXAMPLE III

Hydration of the cyclic allene a. Cyclopentadeca-1,2-diene (1.67 g, prepared as in Example II in acetone (20 ml) was stirred with a mixture of concentrated sulphuric acid (1.8 g), mercury (II) sulphate (0.16 g) and water (2 ml) for 10 hours. The reaction mixture was diluted with water (50 ml) and extracted with pentane (2 × 25 ml). The extracts were washed with saturated sodium bicarbonate solution, dried and the solvent removed under reduced pressure. The residue (1.6 g) was shown to contain crude 3-hydroxycyclopentadecene.

b. Cyclopentadeca-1,2-diene (2.84 g), mercuric nitrate (0.26 g), water (2 ml), acetone (20 ml) and hydroquinone (a few crystals) were stirred under nitrogen for 4 hours at 70° C. The required alcohol was isolated in 90% yield.

EXAMPLE IV

Cyclopentadecen-3-one a. 3-Hydroxycyclopentadecene (1.3 g, prepared as in Example III) in ether (6 ml) was added to a solution of sodium dichromate (1.3g) in water (4.4 ml) containing concentrated sulphuric acid (1.0 ml) and the mixture was stirred at room temperature for 4 hours. The ether was then separated from the aqueous layer when was then extracted with ether (2 × 10 ml). The ether solutions were combined, washed with sodium bicarbonate solution, dried and evaporated under reduced pressure. The residue (0.72 g) was shown to consist of a crude 1:1 mixture of the cis and trans isomers of the desired alpha, beta-unsaturated ketone.

b. 3-Hydroxycyclopentadecene (20.1 g) in dried n-heptane was stirred at room temperature and a total of 100 g manganese dioxide was added in four batches of 50, 25, 15 and 10 g respectively over a period of 6 hours. After 22 hours the conversion as indicated by GLC was 100%. The mixture was filtered and the filtrate was then stirred with active charcoal and refiltered. The solvent was then removed from the filtrate under reduced pressure to yield the required product.

EXAMPLE V

3-Methylcyclopentadecanone (muscone)

Cyclopentadecen-3-one (0.5 g, prepared as in Example IV) in ether (4.5 ml) was added over a period of 45 minutes at 10° C to a solution of methyl magnesium iodide (3.24 mmole) in ether (4.6 ml) containing copper (I) chloride (0.0162 g). Stirring was continued for one hour at 10° C and a further 2.5 hours at room temperature. 10% Hydrochloric acid (3.2 ml) was added to the mixture which was then stirred until the magnesium salts had dissolved. The aqueous layer was removed and the organic layer was washed with water (5 ml ) followed by sodium bicarbonate solution. The dried solution was then evaporated under reduced pressure to yield 0.4 g of product which was shown by GLC and mass spectroscopic analysis to contain 55% muscone.

What is claimed is:

1. A process for preparing a saturated cyclic ketone having the formula

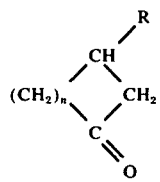

wherein R is hydrogen or $C_1$ to $C_6$ alkyl, and $n$ is an integer of from 9 to 17, which process comprises:

a. reacting a cyclic olefin of the formula

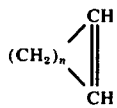

with a dihalocarbene in the presence of a catalyzing amount of an onium salt, b. dehalogenating the dihalobicyclic compound formed in step (a) thereby producing a cyclic allene of the formula

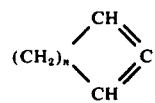

c. hydrating and oxidizing the cyclic allene formed in step (b) thereby producing a cyclic unsaturated ketone of the formula

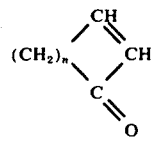

d. converting the double bond of said unsaturated cyclic ketone formed in step (c) to a single bond thereby producing the aforesaid saturated cyclic ketone.

2. The process of claim 1 wherein the dihalocarbene in step (a) is generated in situ by the reaction of a haloform with an alkali metal hydroxide.

3. The process of claim 2 wherein the onium salt is a quaternary ammonium, quaternary phosphonium or ternary sulphonium salt.

4. The process according to claim 3 wherein the dehalogenation in step (b) is accomplished by treating the dihalobicyclic compound formed in step (a) with activated magnesium or a lithium alkyl.

5. The process of claim 3 wherein the hydration and oxidation in step (c) are accomplished by reacting the cyclic allene with borine, followed by reaction of the resulting product with alkaline hydrogen peroxide solution to effect simultaneous hydrolysis and oxidation of said product.

6. The process of claim 4 wherein the hydration in step (c) is accomplished by hydrating the cyclic allene with water in the presence of a mercury (II) compound and the oxidation is accomplished by treating the resulting alcohol product with an oxidizing system selected from (a) a chromium (VI) compound under acidic conditions and (b) a manganese (IV) compound under neutral conditions.

7. The process of claim 1 wherein the unsaturated ketone in step (d) is converted to a saturated cyclic ketone wherein the R substituent is alkyl.

8. The process of claim 6 wherein the mercury (II) compound is mercuric nitrate and hydration is carried out in the absence of mineral acid.

9. The process of claim 4 wherein the unsaturated cyclic ketone in step (d) is treated with an alkyl Grignard reagent in the presence of a copper (I) halide as catalyst, followed by hydrolysis.

10. The process of claim 1 wherein the reaction in step (a) is carried out in a two phase aqueous/organic solvent system utilizing a halogenated hydrocarbon as the organic solvent.

11. The process of claim 10 wherein the onium salt catalyst is tri-sec-octyl methylammonium chloride, tetramethyl phosphonium iodide, sec-hexadecyl sec-dodecyl ethylsulphonium ethylsulphate, di-dodecyl ethylsulphonium ethylsulphate or di-hexadecyl ethylsulphonium ethylsulphate.

12. The process of claim 4 wherein the hydration of the cyclic allene in step (c) is accomplished by reacting the allene with formic acid in the presence of a mercury (II) compound, then hydrolyzing the formate ester thus formed under basic conditions to form the alcohol.

* * * * *